(12) United States Patent
Wolffenbuttel et al.

(10) Patent No.: US 11,933,721 B2
(45) Date of Patent: Mar. 19, 2024

(54) AUTOMOTIVE EXHAUST ULTRAVIOLET SPECTROSCOPY

(71) Applicant: Ford Global Technologies, LLC, Dearborn, MI (US)

(72) Inventors: Reinoud Wolffenbuttel, Leidschendam (NL); David Bilby, Royal Oak, MI (US); Nathan Kempema, Grosse Pointe Farms, MI (US); Jacobus Hendrik Visser, Farmington Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 74 days.

(21) Appl. No.: 17/727,177

(22) Filed: Apr. 22, 2022

(65) Prior Publication Data

US 2023/0341319 A1    Oct. 26, 2023

(51) Int. Cl.
*G01N 21/33* (2006.01)
*G01N 21/63* (2006.01)
*G01N 33/00* (2006.01)

(52) U.S. Cl.
CPC .......... *G01N 21/33* (2013.01); *G01N 21/631* (2013.01); *G01N 33/0047* (2013.01); *G01N 2201/062* (2013.01)

(58) Field of Classification Search
CPC . G01N 21/33; G01N 21/631; G01N 2201/062
See application file for complete search history.

(56) References Cited

U.S. PATENT DOCUMENTS

| 7,238,328 | B2 | 7/2007 | Buhr |
| 8,395,776 | B2 | 3/2013 | Birks et al. |
| 10,207,927 | B2 | 2/2019 | Andersen et al. |
| 11,073,480 | B2 | 7/2021 | Rusanov et al. |
| 2004/0108197 | A1* | 6/2004 | Buhr .................... G01N 21/631 422/186.3 |
| 2009/0137055 | A1 | 5/2009 | Bognar |
| 2020/0225126 | A1* | 7/2020 | Sur .................... G01N 21/8507 |
| 2023/0341352 | A1* | 10/2023 | Bilby .................... G01N 27/49 |

FOREIGN PATENT DOCUMENTS

| CN | 102445415 | 7/2013 |
| CN | 108931490 | 12/2018 |

* cited by examiner

*Primary Examiner* — David P Porta
*Assistant Examiner* — Casey Bryant
(74) *Attorney, Agent, or Firm* — Burris Law, PLLC (57) ABSTRACT

A method for spectroscopically detecting a chemical in a gas sample includes illuminating the gas sample with ultraviolet light and photolyzing a first chemical in the gas sample to generate a photolyzed gas sample and spectroscopically detecting a second chemical in the photolyzed gas sample. The second chemical has an optical absorption range within a respective optical absorption range of the first chemical.

20 Claims, 6 Drawing Sheets

AUTOMOTIVE EXHAUST ULTRAVIOLET SPECTROSCOPY

FIELD

The present disclosure relates to measuring automotive exhaust emissions, particularly with light spectroscopy.

BACKGROUND

The statements in this section merely provide background information related to the present disclosure and may not constitute prior art.

Exhaust gas sensors detect chemical species in exhaust gasses of vehicles, such as nitrogen dioxide. The chemical species are useful to detect for government regulations and tailpipe emissions standards. A set of data collected by the sensors may indicate one or more different chemical species, and isolating a specific chemical species present in the exhaust gas may not be conclusively determined from the data alone. Moreover, certain chemical species may cause noise in data that would indicate other chemical species that are more desirable to detect.

The present disclosure addresses challenges related to detecting chemical species in exhaust gas.

SUMMARY

This section provides a general summary of the disclosure and is not a comprehensive disclosure of its full scope or all of its features.

In one form, a method for spectroscopically detecting a chemical in a gas sample includes illuminating the gas sample with ultraviolet light and photolyzing a first chemical in the gas sample to generate a photolyzed gas sample and spectroscopically detecting a second chemical in the photolyzed gas sample. The second chemical has an optical absorption range within a respective optical absorption range of the first chemical.

In variations of the method, which may be implemented individually or in combination: the second chemical is one of formaldehyde, benzene, toluene, and xylene; the method further includes actuating a light-emitting diode to illuminate the gas sample with ultraviolet light; transmitting the ultraviolet light from the light-emitting diode to the gas sample via a fiber optic cable; the first chemical is nitrogen dioxide, and the method further includes photolyzing the nitrogen dioxide in the gas sample to nitrogen oxide and detecting formaldehyde in the photolyzed gas sample; the first chemical is ozone, and the method further includes photolyzing the ozone in the gas sample to molecular oxygen and detecting at least one of benzene, toluene, and xylene in the photolyzed gas sample; emitting a light beam having a frequency within a specified frequency range to illuminate the gas sample, the specified frequency range selected to photolyze the gas sample and to spectroscopically detect the second chemical; I splitting the light beam with a lens into a first light beam and a second light beam, the first light beam including ultraviolet light to photolyze the gas sample and the second light beam configured to spectroscopically detect the second chemical; transmitting the emitted light beam with a fiber optic cable; placing the photolyzed gas sample in a gas chamber and spectroscopically detecting the second chemical in the gas chamber; spectroscopically detecting the second chemical includes illuminating the photolyzed gas sample with light emitted at a specified frequency range, receiving light unabsorbed by the photolyzed gas sample, and detecting the second chemical based on the specified frequency range of the emitted light and a frequency range of the received light; placing the gas sample in a gas chamber and illuminating the gas sample with ultraviolet light in the gas chamber.

In another form, a system for spectroscopically detecting a specified chemical in a gas sample includes a gas chamber, an ultraviolet light source configured to photolyze a background chemical in the gas sample, and a spectroscopic sensor in communication with the gas chamber. The spectroscopic sensor is configured to detect the specified chemical in the photolyzed gas sample in the gas chamber. The specified chemical has an optical absorption range within a respective optical absorption range of the background chemical.

In variations of the system, which may be implemented individually or in combination: the detected chemical is one of formaldehyde, benzene, toluene, and xylene; the background chemical is one of nitrogen dioxide or ozone; a fiber optic cable connects the ultraviolet light source to the gas sample; the fiber optic cable is connected to the gas chamber to photolyze the gas sample in the gas chamber; a gas inlet is connected to the gas chamber, and the ultraviolet light source is configured to photolyze the gas sample in the gas inlet and the gas inlet introduces the photolyzed gas sample to the gas chamber; the spectroscopic sensor is disposed in the gas chamber; the spectroscopic sensor is configured to detect the specified chemical by illuminating the photolyzed gas sample with light emitted at a specified frequency range, receiving light unabsorbed by the photolyzed gas sample, and detecting the specified chemical based on the specified frequency range of the emitted light and a frequency range of the received light.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
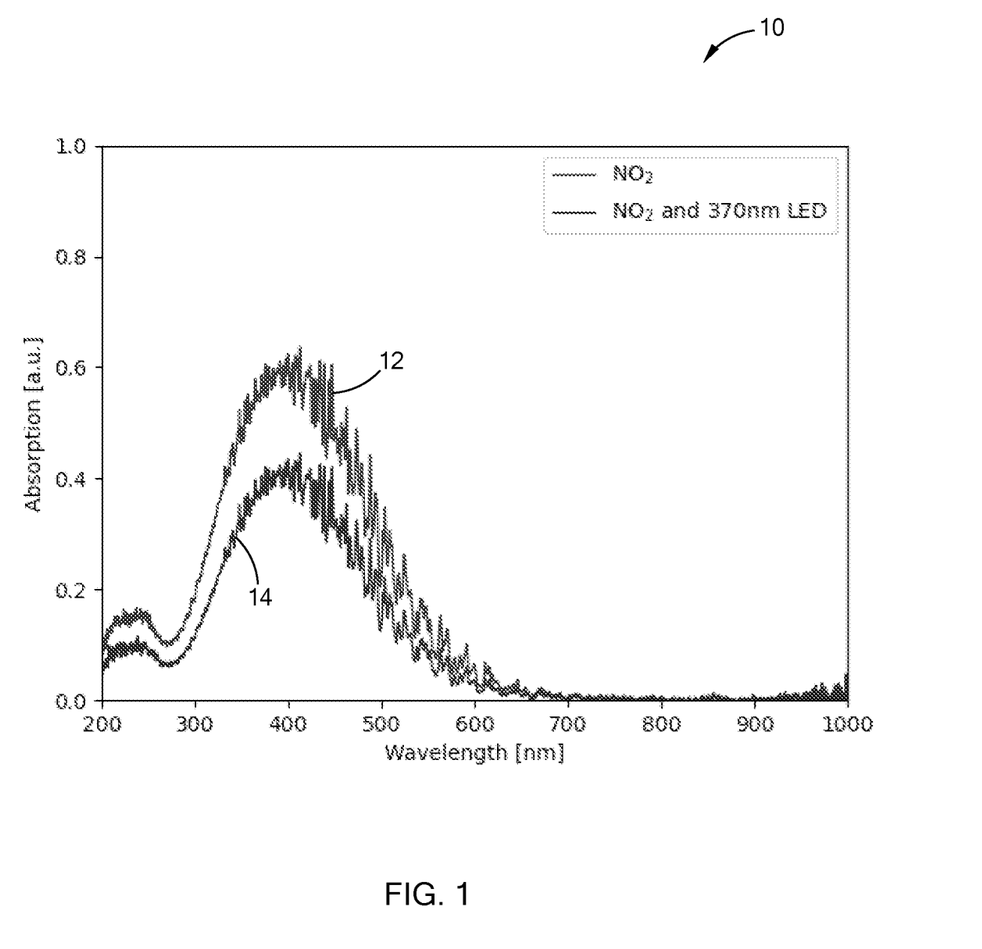
FIG. 1 is a chart of light absorption of a chemical species in an exhaust gas sample according to the present disclosure.

With reference to FIG. 1, a chemical spectroscopy chart 10 shows plots 12, 14 of optical absorption ranges of light a chemical species in exhaust gas samples. An "optical absorption range" is an amount of light absorbed by a chemical species at a plurality of specified wavelengths of light within a range of wavelengths. A first plot 12 shows light absorption by nitrogen dioxide in a gas sample, and a second plot 14 shows nitrogen dioxide in a gas sample photolyzed by ultraviolet light. In the context of this disclosure, a "photolyzed" gas sample is a sample of a gas that has been illuminated with light to photolyze background chemicals in the gas, and an "unphotolyzed" gas sample is a sample of a gas that has not been illuminated with light to photolyzed chemicals in the gas. To "photolyze" a gas means to apply light to the gas in order to initiate or augment a chemical reaction that changes molecules of the gas into different molecules. In one form, nitrogen dioxide ($NO_2$) photolyzes into nitrogen oxide (NO) and monomolecular oxygen (O) when illuminated with ultraviolet light:

$$NO_2 + UV\ light \rightarrow NO + O$$

The chart 10 shows an amount of absorption on the vertical axis, measured from 0 to 1 where 0 means no absorption at a specific wavelength of light and 1 means complete absorption of the specific wavelength of light. The chart 10 shows a wavelength of the light on the horizontal axis, measured in nanometers (nm).

The plots 12, 14 of the optical absorption range of the chemical species in the gas sample and the photolyzed gas sample indicate an amount of the chemical species present. That is, a higher value on the chart 10 is interpreted as having more of the chemical species in the sample. The plot 12 of the absorption of nitrogen dioxide in the unphotolyzed gas sample has higher values of absorption than the plot 14 of the absorption of nitrogen dioxide in the photolyzed gas sample. Thus, by illuminating the gas sample to photolyze the nitrogen dioxide, the photolyzed gas sample has less nitrogen dioxide than the unphotolyzed gas sample. The gas sample is illuminated in one form with a light-emitting diode that light in a specified frequency range designed to photolyze the nitrogen dioxide. In one form, the specified frequency range is 200-500 nm, and the light-emitting diode emits light having a wavelength of 370 nm. This range is referred to as an "ultraviolet" range because the wavelengths of the light are shorter than that of visible violet light, and light having wavelengths in this range is "ultraviolet light." Alternatively, a different light source is actuated to emit the ultraviolet light, such as a laser.

A conventional chemical spectroscopy sensor (e.g., an optical sensor, also referred to herein as a spectroscopic sensor), such as described below and shown in FIGS. 2-4, detects one or more chemical species in the gas sample. In this context, "chemical spectroscopy" means to detect chemicals by the specific wavelengths of light absorbed by the chemicals. Each chemical species absorbs light in a specific range of wavelengths, and the sensor detects the chemical species by illuminating the gas sample and receiving unabsorbed light from the gas sample. A difference between wavelengths of the emitted light and wavelengths of the received light indicates light absorbed by the chemicals in the gas sample (an "optical absorption range"), and thus indicates amounts and types of chemicals in the gas sample. The optical absorption range of the received light is compared to known optical absorption ranges to identify the chemical species. In one form, conventional data fitting techniques (such as regression) are used to compare the optical absorption range of the received light to the optical absorption ranges of chemical species. Differentiating between chemical species with similar absorption ranges (such as $NO_2$ and formaldehyde) may be difficult with such techniques, particularly when the background chemical species absorbs light more strongly and is present in higher concentrations than a desired chemical species. Photolyzing the background chemical species reduces the amount of the background chemical, improving detection of the desired chemical species.

The chart 10 of FIG. 1 shows an optical absorption range of nitrogen dioxide, and different chemical species have respective specific optical absorption ranges. In one form, formaldehyde has a similar absorption range as nitrogen dioxide, and the chemical spectroscopy sensor, upon receiving the unabsorbed light, may not be able to distinguish between an amount of nitrogen dioxide and an amount of formaldehyde in the gas sample. Thus, in order to detect the formaldehyde, the gas sample is photolyzed to reduce the amount of background nitrogen dioxide in the gas sample, reducing ambiguity of the chemicals detected by the sensor. In this manner, spectroscopically detecting formaldehyde in the photolyzed gas sample is more likely than spectroscopically detecting formaldehyde in the unphotolyzed gas sample. In addition to photolyzing the background nitrogen dioxide in the gas sample, the emitted light may be absorbed by other chemicals, and the absorption indicates a chemical species other than nitrogen dioxide, spectroscopically detecting the other chemical.

In another form, the photolyzed background chemical is ozone ($O_3$) that photolyzes into molecular oxygen ($O_2$) and monoatomic oxygen (O):

$$O_3 + UV\ light \rightarrow O_2 + O$$

In such a form, the chemical species detected with the spectroscopic sensor has an optical absorption range within the optical absorption range of ozone, such as benzene, toluene, and xylene (BTX gasses). Thus, the chemical spectroscopy sensor detects formaldehyde, benzene, toluene, and xylene more readily in the photolyzed gas sample than in the unphotolyzed gas sample. A discussion of ultraviolet photolysis of atmospheric chemical species, including nitrogen dioxide and ozone described above, is disclosed in lecture notes from Jose-Luis Jimenez, available at http://cires1.colorado.edu/jimenez/AtmChem/.

Figure 2:
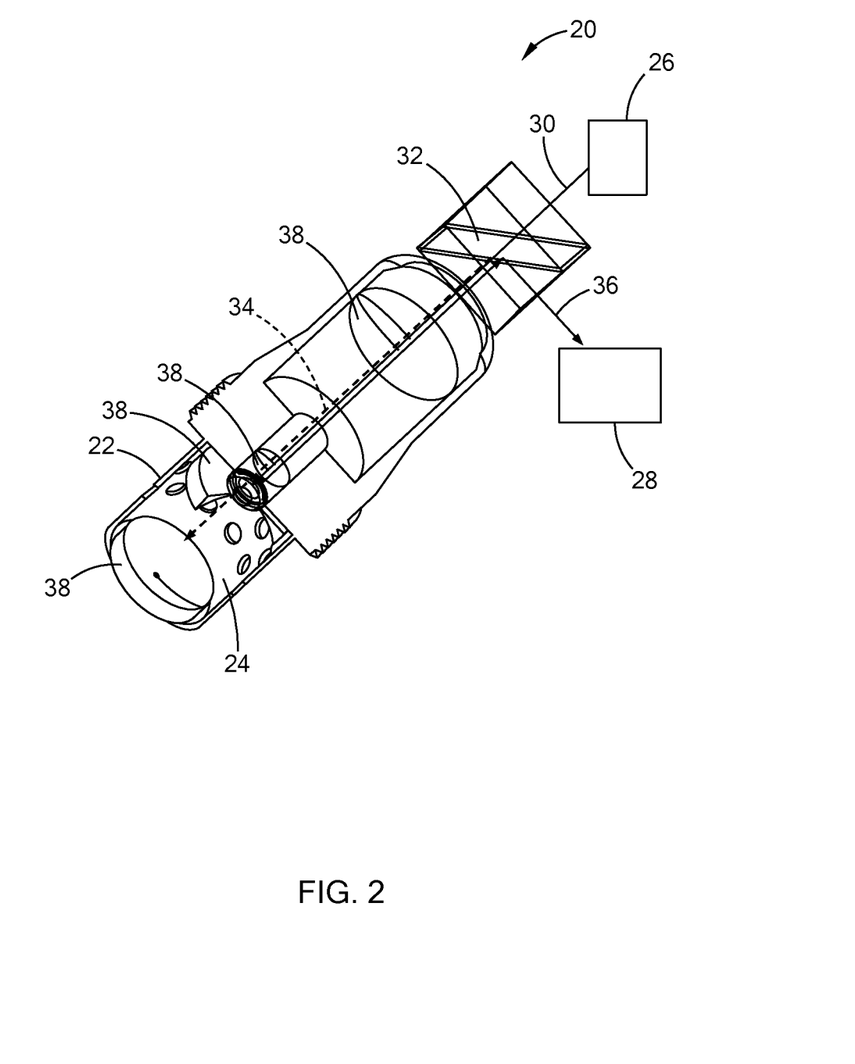
FIG. 2 is a perspective view of an exhaust gas sensor according to the present disclosure.

With reference to FIG. 2, an exhaust gas sensor 20 detects specified chemical species in a photolyzed gas sample. The exhaust gas sensor 20 includes a gas inlet 22, a gas chamber 24, an ultraviolet light source 26, and a spectroscopic sensor 28. The exhaust gas sensor 20 is configured to detect one or more specified chemical species in an exhaust gas sample, particularly species that have optical absorption ranges within optical absorption ranges of nitrogen dioxide and ozone. The exhaust gas sensor 20 is disposed in an exhaust pipe (not shown) through which exhaust gasses from an internal combustion engine flow to a tailpipe. The exhaust gasses are outputs from fuel combusted in the internal combustion engine, such as gasoline, ethanol, and diesel.

The gas inlet 22 provides exhaust gas to the gas chamber 24. In the form of FIG. 2, the gas inlet 22 is a series of holes that allow exhaust gas from the exhaust pipe into the gas chamber 24, and the ultraviolet light source 26 photolyzes the exhaust gas in the gas chamber 24. In another form not shown in FIG. 2, the gas inlet 22 is a separated from the gas chamber 24, and the ultraviolet light source 26 photolyzes the gas sample in the gas inlet 22. The gas inlet 22 in such a form then introduces the photolyzed gas sample to the gas chamber 24 to detect the chemical species.

The exhaust gas sensor 20 includes the spectroscopic sensor 28 in communication with the gas chamber 24. The spectroscopic sensor 28 is configured to detect the chemical species based on light absorption by the gas sample. In one form, a light source (that may include the ultraviolet light source 26) illuminates the photolyzed gas sample with light emitted at a specified frequency range. Light unabsorbed by the photolyzed gas sample is received by a photodetector of the spectroscopic sensor 28. Based on the specified frequency range of the emitted light and a frequency range of the received light, the spectroscopic sensor 28 (or a controller in communication with the spectroscopic sensor) determines an amount of one or more specified chemical species in the gas sample. That is, the spectroscopic sensor 28 determines the wavelengths absorbed by the chemical species in the gas sample, and based on the ranges of absorbed wavelengths, the spectroscopic sensor 28 determines the chemicals present in the gas sample.

In the form of FIG. 2, a single light beam 30 from the light source 26 is split with a beam splitter 32 into a first light beam 34 and a second light beam 36. The first light beam 34, shown in dashed lines, includes ultraviolet light to photolyze the gas sample. The second light beam 36, shown in a solid line, includes a broad spectrum of frequencies to spectroscopically detect chemicals in the photolyzed gas sample. The beam splitter 32 is a conventional device that separates one or more beams of light from the light source 26, such as a prism. The beam splitter 32 is configured to separate light in an ultraviolet light range into the first light beam 34. By splitting the light beam 30, a single light source 26, such as a light-emitting diode, provides light to both photolyze the gas sample and spectroscopically detect specified chemicals. In addition to the beam splitter 32, one or more lenses or mirrors, collectively "focusing devices" 38, direct the light beams 34, 36 to the exhaust sample and seal the exhaust gas sample from other parts of the exhaust gas sensor 20.

Figure 3:
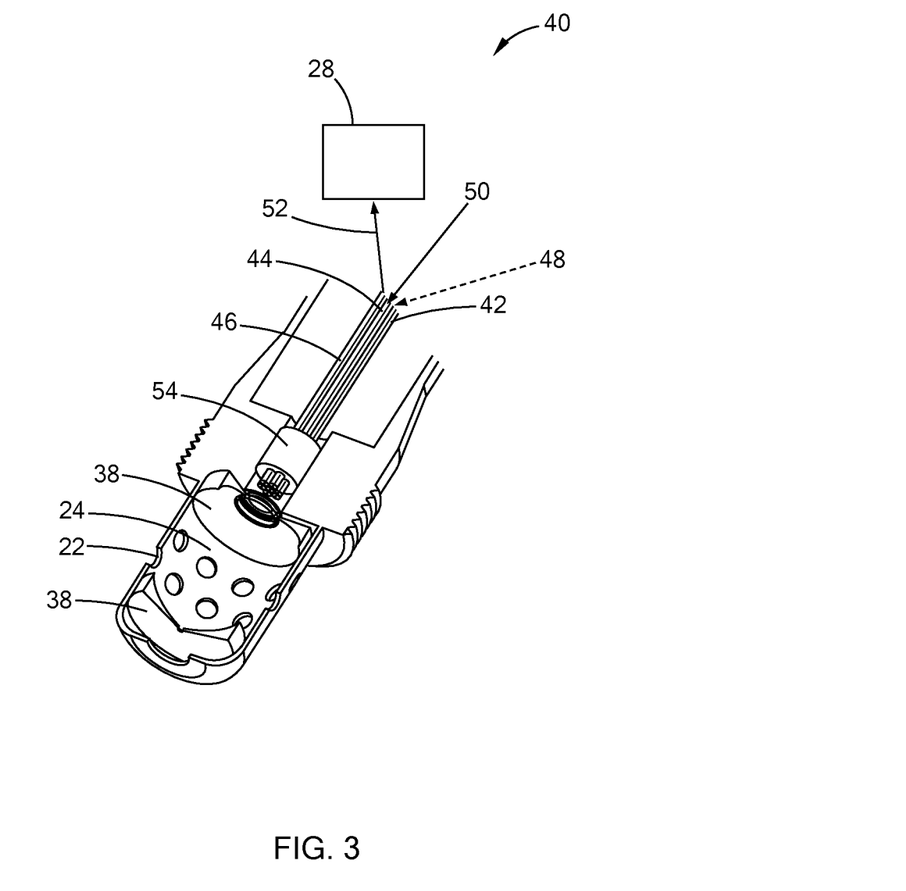
FIG. 3 is a perspective view of another exhaust gas sensor according to the present disclosure.

With reference to FIG. 3, an exhaust gas sensor 40 includes a plurality of fiber optic cables 42, 44, 46 that transmit light to the gas sample. A first fiber optic cable 42 transmits ultraviolet light 48 from an ultraviolet light source (such as a light-emitting diode) to photolyze the gas sample in the gas chamber 24. A second fiber optic cable 44 transmits light 50 from a broad-spectrum light source that the photolyzed gas sample absorbs for spectroscopy. A third fiber optic cable 46 transmits light 52 unabsorbed by the gas sample to the spectroscopic sensor 28 to detect the chemicals in the photolyzed gas samples. A gas-impermeable seal 54 prevents the exhaust gas sample from reaching other parts of the exhaust gas sensor 20. Using the plurality of fiber optic cables 42, 44, 46 allows the use of multiple dedicated light sources to provide light at specified ranges of wavelengths for photolyzing and spectroscopically analyzing the gas sample.

Figure 4:
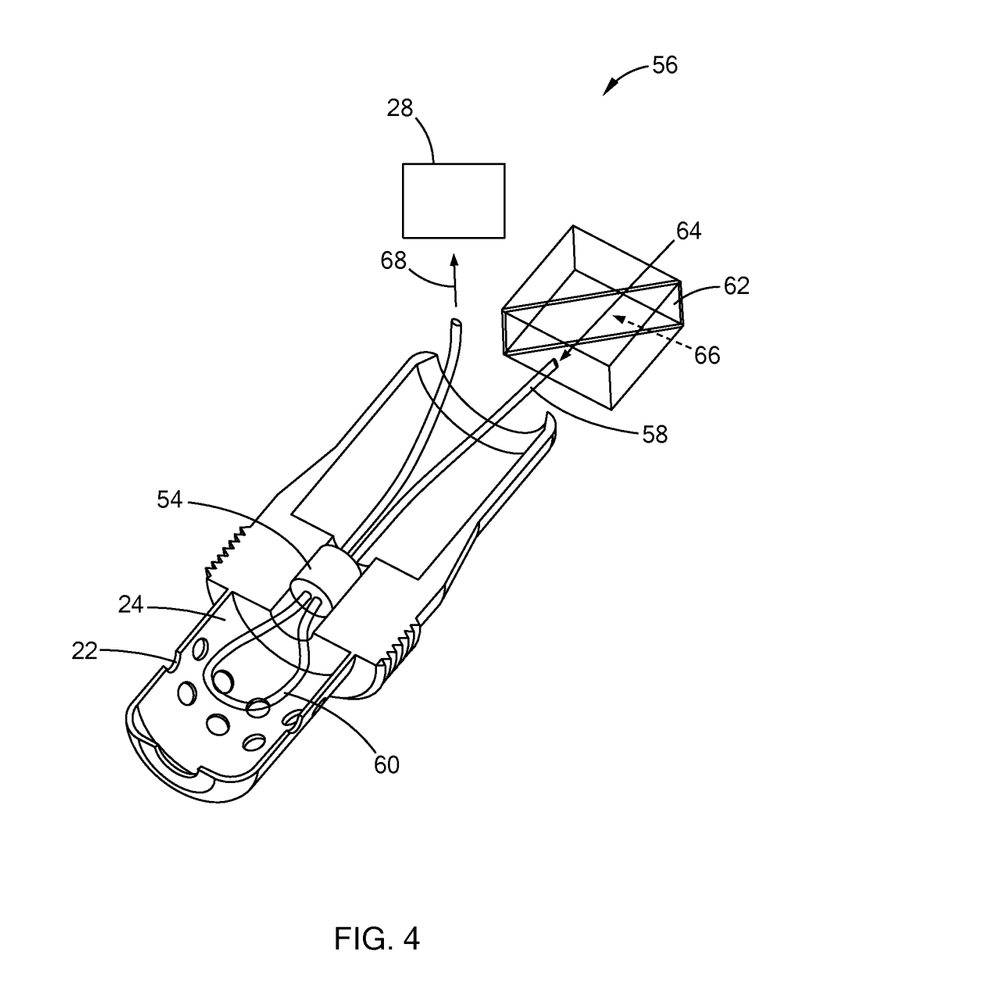
FIG. 4 is a perspective view of another exhaust gas sensor according to the present disclosure.

With reference to FIG. 4, an exhaust gas sensor 56 includes a single fiber optic cable 58 with a transparent outer surface 60 to illuminate the gas sample in the gas chamber 24. A beam splitter 62 combines a broad-spectrum beam of light 64 with a beam of ultraviolet light 66 into the single fiber optic cable 58 to photolyze the exhaust gas sample and to spectroscopically detect chemical species in the gas sample. The light beams 64, 66 are emitted from respective light sources, such as the ultraviolet light source 26 described above and a broad-spectrum light source. The gas sample is provided to the gas chamber 24, and the fiber optic cable 58 emits ultraviolet light 66 from the light source though the transparent outer surface 60 to photolyze the gas sample. Then, light 68 unabsorbed by the photolyzed gas sample is sent through the fiber optic cable to the spectroscopic sensor 28 to detect chemicals in the gas sample. By placing the fiber optic cable 58 directly in the gas chamber, the emitted ultraviolet light 66 more readily reaches the exhaust gas, photolyzing the sample more quickly and more readily reducing the nitrogen dioxide and ozone in the gas sample. As also shown in FIG. 4, a gas-impermeable seal 54 prevents the exhaust gas sample from reaching other parts of the exhaust gas sensor 56.

Figure 5:
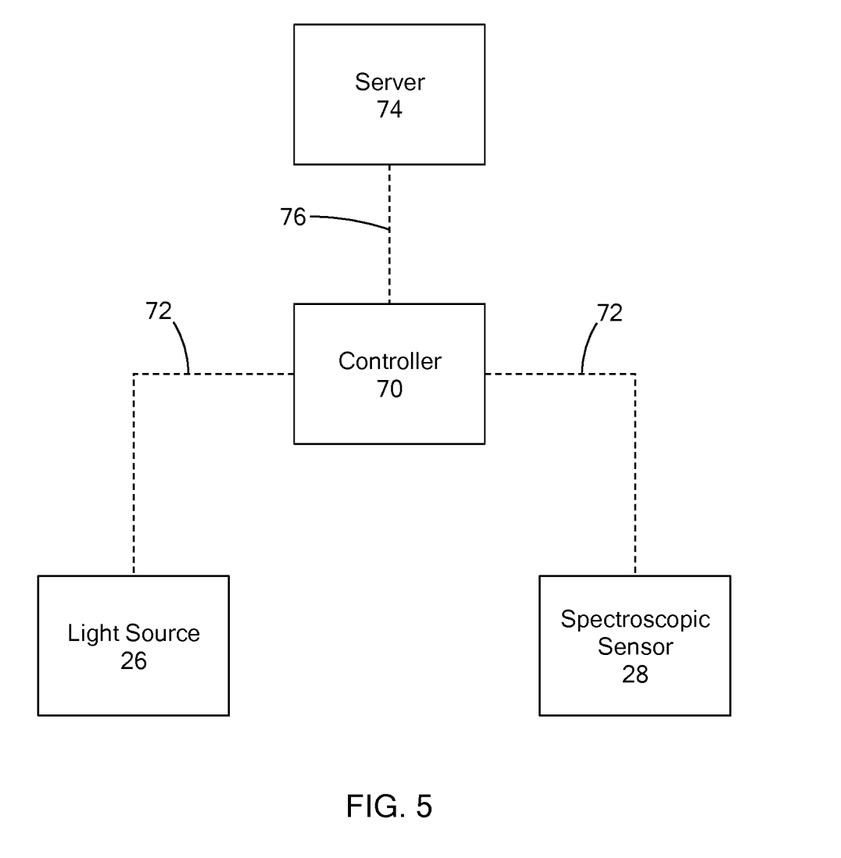
FIG. 5 is a block diagram of a controller that operates the exhaust gas sensor according to the present disclosure.

With reference to FIG. 5, a controller 70 controls the light source 26 and the spectroscopic sensor 28 to collect data about chemical species in the exhaust gas sample. The controller 70 provides instructions to the light source 26 to emit light to photolyze the gas sample in the gas chamber 24 of the exhaust gas sensor 20, 40, 56. The controller 70 collects data from the spectroscopic sensor, such as wavelength data of received unabsorbed light. Upon collecting the data, the controller 70 determines amounts of the chemical species present in the exhaust gas sample based on conventional spectroscopic techniques. In one example, the controller 70 determines an amount of formaldehyde in the exhaust gas sample in which background nitrogen dioxide is photolyzed. In another example, the controller 70 determines an amount of at least one of benzene, toluene, and xylene in the exhaust gas sample in which background ozone is photolyzed. The controller 70 communicates with the light source 26 and the sensor 28 via a communications path 72, such as a bus, a wired network, or a wireless network. The controller 70 stores the collected chemical species data in a memory. In one form, the controller 70 transmits the collected data to an external server 74 via a wireless communications path 76 that tracks chemical emissions data from a plurality of vehicles. The controller 70 is housed in the vehicle in which the exhaust gas sample is collected.

Figure 6:
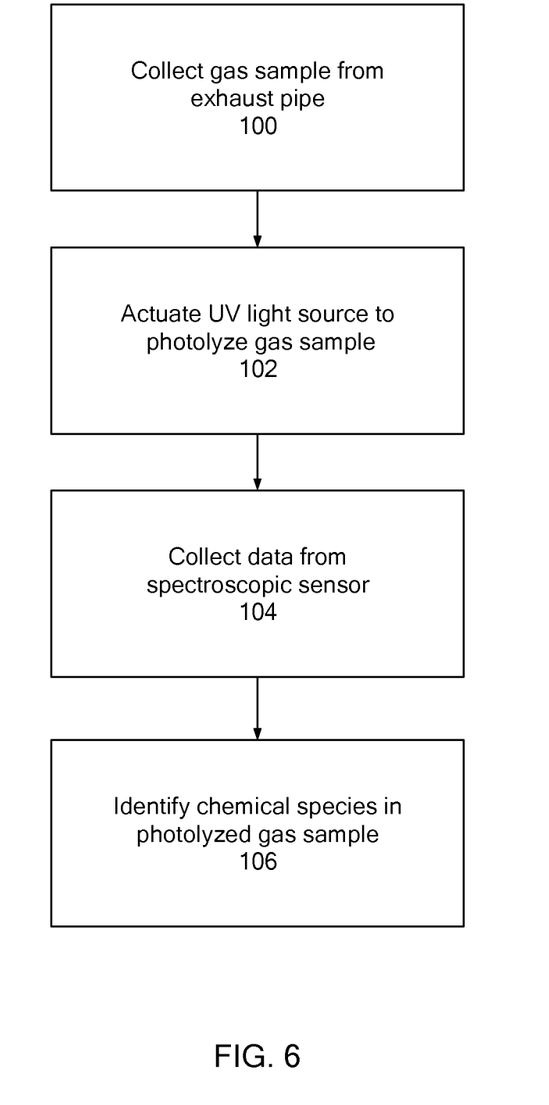
FIG. 6 is a block diagram of a process for detecting chemical species in the exhaust gas sample with the exhaust gas sensor according to the present disclosure.

FIG. 6 is a block diagram of an example process for identifying a specified chemical species in an exhaust gas sample. The process begins in a block 100, in which a gas sample is collected from an exhaust pipe of a vehicle. An exhaust gas sensor is disposed in the exhaust pipe to collect the gas sample. The gas sample is collected via a gas inlet 22 of an exhaust gas sensor 20, 40, 56 that directs the gas sample to a gas chamber 24.

Next, in a block 102, a controller 70 actuates an ultraviolet light source 26 to photolyze the gas sample. As described above, photolyzing the gas sample reduces respective amounts of background chemicals such as nitrogen dioxide and ozone, allowing other chemical species to be detected by an exhaust gas sensor 20, 40, 56, such as formaldehyde, benzene, toluene, and xylene. The ultraviolet light source 26 in one form is a light-emitting diode.

Next, in a block 104, the controller 70 collects data from a spectroscopic sensor 28. As described above, the photolyzed gas sample is illuminated with broad spectrum light, and the spectroscopic sensor 28 detects light that is not absorbed by the gasses in the gas sample. The spectroscopic sensor 28 transmits data indicating wavelengths of the unabsorbed light to the controller 70 via a communications bus 72.

Next, in a block 106, the controller 70 identifies amounts of one or more chemical species in the photolyzed gas sample. As described above, chemicals have specific optical absorption ranges that may overlap with optical absorption ranges of the background chemicals. By reducing the amounts of the background chemicals, the specified chemicals are more easily detected, such as formaldehyde, benzene, toluene, and xylene. The controller 70 stores data indicating the amounts of the specified chemical species in a memory. Following the block 106, the process ends.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for spectroscopically detecting a chemical in a gas sample, the method comprising:
    illuminating the gas sample with ultraviolet light and photolyzing a first chemical in the gas sample to generate a photolyzed gas sample; and
    spectroscopically detecting a second chemical in the photolyzed gas sample,
    wherein the second chemical has an optical absorption range within a respective optical absorption range of the first chemical.

2. The method of claim 1, wherein the second chemical is one of formaldehyde, benzene, toluene, and xylene.

3. The method of claim 1, further comprising actuating a light-emitting diode to illuminate the gas sample with ultraviolet light.

4. The method of claim 3, further comprising transmitting the ultraviolet light from the light-emitting diode to the gas sample via a fiber optic cable.

5. The method of claim 1, wherein the first chemical is nitrogen dioxide, and the method further comprises photolyzing the nitrogen dioxide in the gas sample to nitrogen oxide and detecting formaldehyde in the photolyzed gas sample.

6. The method of claim 1, wherein the first chemical is ozone, and the method further comprises photolyzing the ozone in the gas sample to molecular oxygen and detecting at least one of benzene, toluene, and xylene in the photolyzed gas sample.

7. The method of claim 1, further comprising emitting a light beam having a frequency within a specified frequency range to illuminate the gas sample, the specified frequency range selected to photolyze the gas sample and to spectroscopically detect the second chemical.

8. The method of claim 7, further comprising splitting the light beam with a lens into a first light beam and a second light beam, the first light beam including ultraviolet light to photolyze the gas sample and the second light beam configured to spectroscopically detect the second chemical.

9. The method of claim 7, further comprising transmitting the emitted light beam with a fiber optic cable.

10. The method of claim 1, further comprising placing the photolyzed gas sample in a gas chamber and spectroscopically detecting the second chemical in the gas chamber.

11. The method of claim 1, wherein spectroscopically detecting the second chemical includes illuminating the photolyzed gas sample with light emitted at a specified frequency range, receiving light unabsorbed by the photolyzed gas sample, and detecting the second chemical based on the specified frequency range of the emitted light and a frequency range of the received light.

12. The method of claim 1, further comprising placing the gas sample in a gas chamber and illuminating the gas sample with ultraviolet light in the gas chamber.

13. A system for spectroscopically detecting a specified chemical in a gas sample, the system comprising:
    a gas chamber;
    an ultraviolet light source configured to photolyze a background chemical in the gas sample; and
    a spectroscopic sensor in communication with the gas chamber,
    wherein the spectroscopic sensor is configured to detect the specified chemical in the photolyzed gas sample in the gas chamber,
    wherein the specified chemical has an optical absorption range within a respective optical absorption range of the background chemical.

14. The system of claim 13, wherein the detected chemical is one of formaldehyde, benzene, toluene, and xylene.

15. The system of claim 13, wherein the background chemical is one of nitrogen dioxide or ozone.

16. The system of claim 13, further comprising a fiber optic cable connecting the ultraviolet light source to the gas sample.

17. The system of claim 16, wherein the fiber optic cable is connected to the gas chamber to photolyze the gas sample in the gas chamber.

18. The system of claim 13, further comprising a gas inlet connected to the gas chamber, wherein the ultraviolet light source is configured to photolyze the gas sample in the gas inlet and the gas inlet introduces the photolyzed gas sample to the gas chamber.

19. The system of claim 13, wherein the spectroscopic sensor is disposed in the gas chamber.

20. The system of claim 13, wherein the spectroscopic sensor is configured to detect the specified chemical by illuminating the photolyzed gas sample with light emitted at a specified frequency range, receiving light unabsorbed by the photolyzed gas sample, and detecting the specified chemical based on the specified frequency range of the emitted light and a frequency range of the received light.

* * * * *